US007385708B2

(12) United States Patent
Ackerman et al.

(10) Patent No.: US 7,385,708 B2
(45) Date of Patent: Jun. 10, 2008

(54) METHODS AND SYSTEMS FOR LASER BASED REAL-TIME STRUCTURED LIGHT DEPTH EXTRACTION

(75) Inventors: Jeremy D. Ackerman, Chapel Hill, NC (US); Kurtis P. Keller, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 114 days.

(21) Appl. No.: 10/515,305

(22) PCT Filed: Jun. 9, 2003

(86) PCT No.: PCT/US03/17987

§ 371 (c)(1),
(2), (4) Date: Apr. 27, 2005

(87) PCT Pub. No.: WO03/105289

PCT Pub. Date: Dec. 18, 2003

(65) Prior Publication Data

US 2005/0219552 A1   Oct. 6, 2005

Related U.S. Application Data

(60) Provisional application No. 60/386,871, filed on Jun. 7, 2002.

(51) Int. Cl.
*G01B 11/24* (2006.01)
(52) U.S. Cl. .................................. 356/603
(58) Field of Classification Search .............. 356/603, 356/604, 610
See application file for complete search history.

(56) References Cited

U.S. PATENT DOCUMENTS

| 4,294,544 A | * | 10/1981 | Altschuler et al. .......... 356/610 |
| 5,109,276 A | | 4/1992 | Nudelmann et al. |
| 5,193,120 A | | 3/1993 | Gamache et al. |
| 5,307,153 A | | 4/1994 | Maruyama et al. |
| 5,323,002 A | | 6/1994 | Sampsell et al. |
| 5,371,543 A | | 12/1994 | Anderson |

(Continued)

OTHER PUBLICATIONS

International Search Report in PCT Application No. PCT/US03/17987 (Mar. 22, 2004).

(Continued)

*Primary Examiner*—Gregory J. Toatley, Jr.
*Assistant Examiner*—Juan D Valentin
(74) *Attorney, Agent, or Firm*—Jenkins, Wilson, Taylor & Hunt, P.A.

(57) ABSTRACT

Laser-based methods and systems for real-time structured light depth extraction are disclosed. A laser light source (100) produces a collimated beam of laser light. A pattern generator (102) generates structured light patterns including a plurality of pixels. The beam of laser light emanating from the laser light source (100) interacts with the patterns to project the patterns onto the object of interest (118). The patterns are reflected from the object of interest (118) and detected using a high-speed, low-resolution detector (106). A broadband light source (111) illuminates the object with broadband/light, and a separate high-resolution, low-speed detector (108) detects broadband light reflected from the object (118). A real-time structured light depth extraction engine/controller (110) based on the transmitted and reflected patterns and the reflected broadband light.

64 Claims, 7 Drawing Sheets

U.S. PATENT DOCUMENTS

| | | | |
|---|---|---|---|
| 5,446,798 | A | 8/1995 | Morita et al. |
| 5,452,024 | A | 9/1995 | Sampsell |
| 5,457,493 | A | 10/1995 | Leddy et al. |
| 5,488,431 | A | 1/1996 | Gove et al. |
| 5,489,952 | A | 2/1996 | Gove et al. |
| 5,491,510 | A | 2/1996 | Gove |
| 5,526,051 | A | 6/1996 | Gove et al. |
| 5,532,997 | A | 7/1996 | Pauli |
| 5,541,723 | A | 7/1996 | Tanaka |
| 5,570,135 | A | 10/1996 | Gove et al. |
| 5,608,468 | A | 3/1997 | Gove et al. |
| 5,612,753 | A | 3/1997 | Poradish et al. |
| 5,629,794 | A | 5/1997 | Magel et al. |
| 5,630,027 | A | 5/1997 | Venkateswar et al. |
| 5,699,444 | A | 12/1997 | Palm |
| 5,784,098 | A * | 7/1998 | Shoji et al. .................. 356/608 |
| 5,870,136 | A | 2/1999 | Fuchs et al. |
| 6,341,016 | B1 | 1/2002 | Malione |
| 6,503,195 | B1 | 1/2003 | Keller et al. |

OTHER PUBLICATIONS

Zitnick et al., "Multi-Base Stereo Using Surface Extraction," Visual Interface Inc., (Nov. 24, 1996).

Bajura et al., "Merging Virtual Objects with the Real World: Seeing Ultrasound Imagery within the Patient," Proceedings of SIGGRAPH 92, vol. 2 ( No. 26), p. 203-210, ( Jul. 20, 1992).

Ohbuchi et al., "Incremental Volume Reconstruction and Rendering for 3D Ultrasound Imaging," Visualization in Biomedical Computing, SPIE Proceedings, p. 312-323, ( Oct. 13, 1992).

State et al., "Superior Augmented Reality Registration by Integrating Landmark Tracking and Magnetic Tracking," Computer Graphics Proceedings, Proceedings of SIGGRAPH 96—Annual Conference Series (New Orleans, Louisiana), p. 429-438, ( Aug. 4, 1996).

State et al., "Technologies for Augmented Reality Systems," Computer Graphics Proceedings, Proceedings of SIGGRAPH 96, Annual Conference Series (New Orleans, Louisiana), p. 439-446, ( Aug. 4, 1996).

Garrett et al., "Real-Time Incremental Visualization of Dynamic Ultrasound Volumes Using Parallel BSP Trees," Proceedings of IEEE Visualization of Dynamic Ultrasound Volumes Using Parallel BSP Trees, p. 235-240, ( Oct. 27, 1996).

Jacobs et al., "Managing Latency in Complex Augmented Reality Systems," Proceedings of 1997 Symposium on Interactive 3D Graphics, Annual Conference Series, ACM SIGGRAPH (Providence, Rhode Island), p. 49-54, ( Apr. 27, 1997).

Livingston et al., "Magnetic Tracker Calibration for Improved Augmented Reality Registration," Presence: Teleoperators and Virtual Environments, MIT Press, vol. 6 ( No. 5), p. 532-546, ( Oct. 21, 1997).

Advertisement, "Inspeck 3DC 3D Capturor," Inspeck 3DC 3D Capturor (www.inspeck.com) (1998).

Advertisement, "Virtual 3D High Speed Non-Contact Surface Perception," Virtual 3-D Technologies Corporation (www.virtual3dtech.com), ( Dec. 21, 1998).

Advertisement, "Virtuoso," Visual Interface, Inc., Visual Interface, Inc. (www.visint.com), ( Dec. 21, 1998).

Advertisement, "Virtuoso," Visual Interface, Inc., (1998).

Ohbuchi "Incremental Acquisition and Visualization of 3D Ultrasound Images", Ph.D. Dissertation, UNC-CH Computer Science Technical Report TR95-023, (1993).

Ohbuchi et al. "An Incremental Volume Rendering Algorithm for Interactive 3D Ultrasound Imaging", UNC-CH Computer Science Technical Report TR91-023, (1991).

Fuchs et al. "Towards Performing Ultrasound-Guided Needle Biopsies from Within a Head-Mounted Display", 4th International Conference, VBC '96, Hamburg, Germany, (Sep. 22-25, 1996).

Depiero et al., "3-D Computer Vision Using Structured Light: Design, Calibration and Implementation Issues," The University of Tennessee, p. 1-46, (1996).

Fuchs et al., "Augmented Reality Visualization for Laparoscopic Surgery," MICCAI, vol. 11 ( No. 13), p. 934-943, (Oct. 1998).

State et al., "Case Study: Observing a Volume Rendered Fetus within a Pregnant Patient," IEEE Visualization Conference, 5th ed., p. 364-368, (1994).

* cited by examiner

METHODS AND SYSTEMS FOR LASER BASED REAL-TIME STRUCTURED LIGHT DEPTH EXTRACTION

RELATED APPLICATIONS

This application claims the benefit of U.S. Provisional Patent Application Ser. No. 60/386,871, filed Jun. 7, 2002, the disclosure of which is incorporated herein by reference in its entirety.

GOVERNMENT INTEREST

This invention was made with U.S. Government support under Grant No. DABT63-93-C-0048 from the Advanced Research Projects Agency (ARPA) and under grant number ASC8920219 awarded by the National Science Foundation. The U.S. Government has certain rights in the invention.

TECHNICAL FIELD

The present invention relates to methods and systems for real-time structured light depth extraction. More particularly, the present invention relates to methods and systems for laser-based real-time structured light depth extraction.

BACKGROUND ART

Structured light depth extraction refers to a method for measuring depth that includes projecting patterns onto an object, detecting reflected patterns from the object, and using pixel displacements in the transmitted and reflected patterns to calculate the depth or distance from the object from which the light was reflected. Conventionally, structured light depth extraction has been performed using a slide projector. For example, a series of patterns on individual slides may be projected onto an object. A detector, such as a camera, detects reflected patterns. The pixels in the projected patterns are mapped manually to the pixels in the reflected patterns. Given the position of the projector and the camera and the pixel offsets, the location of the object can be determined.

In real-time structured light depth extraction systems, images are required to be rapidly projected onto an object and detected synchronously with the projection. In addition, the calculations to determine the depth of the object are required to be extremely fast. Currently, in real-time structured light depth extraction systems, an incandescent lamp and a collimator are used to generate a collimated beam of light. In one exemplary implementation, the collimated beam of light is projected onto a pattern generator. The pattern generator reflects the transmitted light onto the object of interest. The reflected pattern is detected by a camera that serves a dual purpose of detecting structured light patterns and reflected broadband light. A specialized image processor receives the reflected images and calculates depth information.

While this conventional structured light depth extraction system may be effective in some situations, incandescent light has poor photonic efficiency when passed through the optics required to image surfaces inside a patient in an endoscopic surgical environment. One reason that incandescent light has been conventionally used for real-time structured light depth extraction systems is that an incandescent lamp was the only type of light source thought to have sufficient power and frequency bandwidth to illuminate objects inside of a patient. Another problem with this conventional structured light depth extraction system is that using a single camera for both broadband light detection and depth extraction is suboptimal since the pixel requirements for broadband light detection are greater than those required for depth extraction, and the required frame speed is greater for depth extraction than for broadband light detection. Using a single camera results in unnecessary data being acquired for both operations. For example, if a high-resolution, high-speed camera is used for depth extraction and broadband light detection, an unnecessary number of images will be acquired per unit time for broadband light detection and the resolution of the images will be higher than necessary for depth extraction. The additional data acquired when using a single camera for both broadband light detection and depth extraction increases downstream memory storage and processing speed requirements.

Accordingly, in light of these difficulties associated with conventional real-time structured light depth extraction systems, there exists a long-felt need for improved methods and systems for real-time structured light depth extraction for an endoscopic surgical environment.

DISCLOSURE OF THE INVENTION

According to one aspect of the invention, a laser-based real-time structured light depth extraction system includes a laser light source for producing a collimated beam of laser light. A pattern generator is optically coupled to the laser light source and generates structured light patterns. Each pattern includes a plurality of pixels, which are simultaneously projected onto an object of interest. A detector is coupled to the light source and is synchronized with the pattern generator for receiving patterns reflected from the object and generating signals based on the patterns. A real-time structured light depth extraction engine/controller is coupled to the detector and the pattern generator for controlling projection and detection of patterns and for calculating, in real-time, depth values of regions in the object based on signals received from the detector. In one implementation, the pattern generator comprises a reflective display, the detector comprises separate cameras for depth extraction and imaging, and the real-time structured light depth extraction engine/controller comprises a general-purpose computer, such as a personal computer, with a frame grabber.

Using a laser light source rather than an incandescent lamp provides advantages over conventional real-time structured light depth extraction systems. For example, laser-based real-time structured light depth extraction systems have been shown to have better photonic efficiency than incandescent-lamp-based real-time structured light depth extraction systems. In one test, the efficiency of a laser-based real-time structured light depth extraction system for endoscopic surgery was shown to have 30% efficiency versus 1% efficiency for incandescent light. This increase in efficiency may be due to the fact that a laser-based real-time structured light depth extraction system may not require a collimator in series with the laser light beam before contacting the pattern generator. In addition, a laser can be easily focused to fit within the diameter of the optical path of an endoscope, while the focal width of an incandescent light beam is limited by the width of the filament, which can be greater than the width of a conventional endoscope. Using a laser for real-time structured light depth extraction in an endoscopic surgical environment may thus allow a smaller diameter endoscope to be used, which results in less trauma to the patient.

Another surprising result of using a laser for real-time structured light depth extraction in an endoscopic surgical environment is that lasers produce sufficient information to extract depth in real time, even given the low power and narrow beam width associated with surgical illumination lasers. As stated above, endoscopic light sources were believed to be required for endoscopic surgical environments because they were the only light sources believed to have sufficient output power for surgical applications. The present inventors discovered that a laser with a beam width of about 2 mm and power consumption of about 5 mW can be used for real-time structured light depth extraction in an endoscopic surgical environment. Such a low power light source can be contrasted with the 40 W lamp used in conventional incandescent-lamp-based real-time structured light depth extraction systems.

In an alternate implementation of the invention, rather than using a laser light source and a separate display, the present invention may include using a self-illuminating display, such as an organic light emitting (OLE) display. Using an OLE display decreases the number of required optical components and thus decreases the size of the real-time structured light depth extraction system. Patterns can be generated and projected simply by addressing the appropriate pixels of the OLE display.

As used herein, the term "real-time structured light depth extraction" is intended to refer to depth extraction that results in rendering of images at a sufficiently high rate for a surgical environment, such as an endoscopic surgical environment. For example, in one implementation, images of an object with depth may be updated at a rate of at least about 30 frames per second.

Accordingly, it is an object of the present invention to provide improved methods and systems for real-time structured light depth extraction in an endoscopic surgical environment.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

Preferred embodiments of the invention will now be explained with reference to the accompanying drawings, of which.

DETAILED DESCRIPTION OF THE INVENTION

Figure 1:
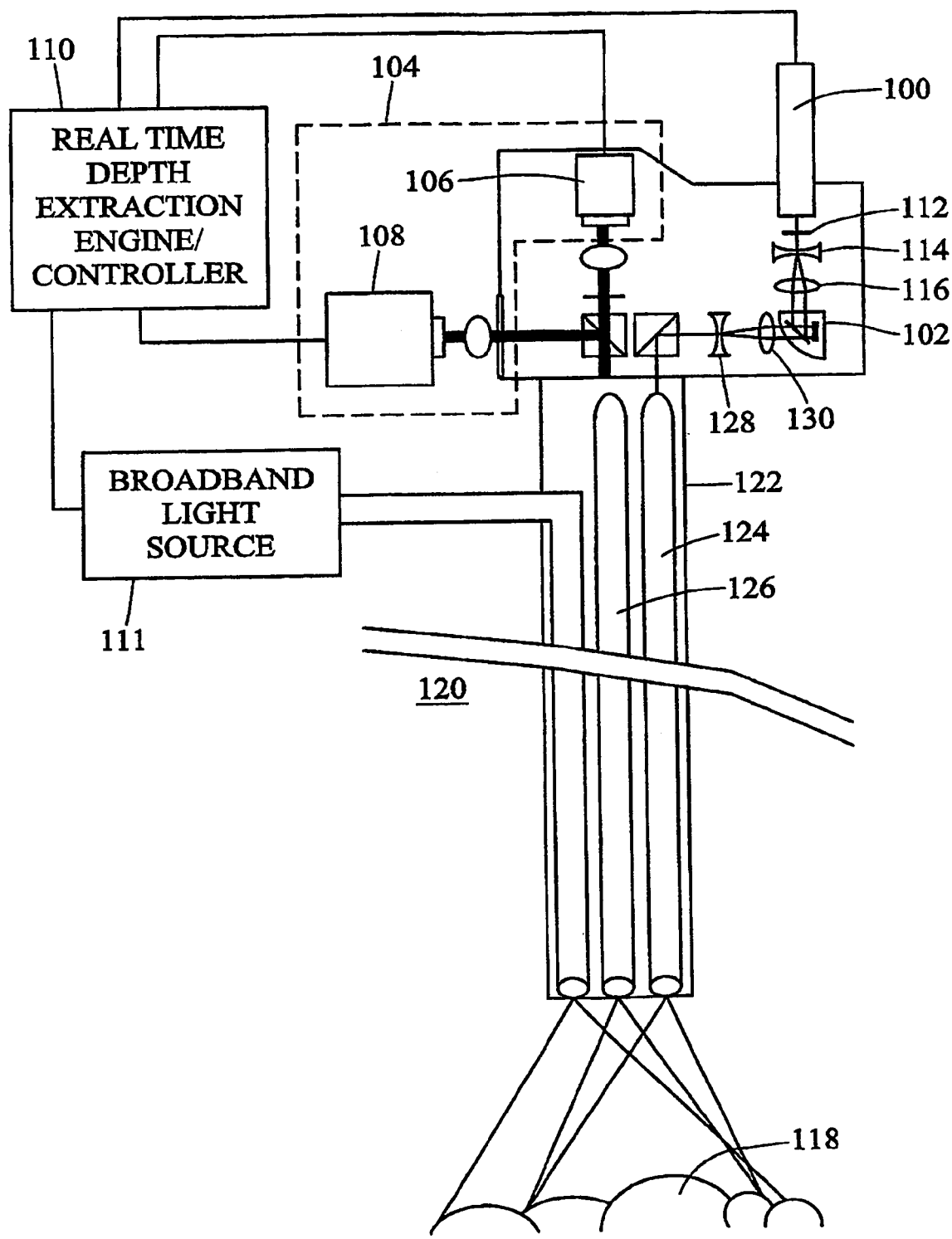
FIG. 1 is a schematic diagram of a laser-based real-time structured light depth extraction system for endoscopic surgery according to an embodiment of the present invention.

FIG. 1 illustrates a system for laser-based real-time structured light depth extraction according to an embodiment of the present invention. Referring to FIG. 1, the system includes a laser light source 100, a pattern generator 102, a detector 104 including cameras 106 and 108 and a real-time depth extraction engine/controller 110. Laser light source 100 may be any suitable laser light source, such as a laser diode. In a preferred embodiment of the invention, when extracting depth for surfaces within the human body, laser light source 100 comprises a narrowband light source of appropriate frequency for a reduced penetration depth and reduced scattering of light by the surfaces being imaged. The frequency range of light emitted from laser light source 100 may be in the visible or non-visible frequency range. A green light source has been found to be highly effective for imaging human and animal tissue. By reducing scattering and penetration of light, features in reflected structured light patterns are more easily detectable.

An exemplary commercially available laser light source suitable for use with embodiments of the present invention is the NT56-499 available from Edmund Optics. The NT-56-499 is a 50 mW fiber coupled solid state laser that operates at 532 nm. Using a laser light source rather than a conventional incandescent lamp reduces the need for collimating optics between a laser light source and the pattern generator. However, collimating optics may be included between laser 100 and display 102 without departing from the scope of the invention.

A broadband light source 111 may be provided for broadband illumination of surfaces within a patient's body so that color images of the surfaces can be generated. An example of a broadband light source suitable for use with embodiments of the present invention is a white incandescent lamp.

Pattern generator 102 may be any suitable device for generating patterns that interact with the light from laser light source 100 and projecting the patterns onto an object of interest. In one exemplary implementation, pattern generator 102 may be a ferro-reflective display. In an alternate embodiment, pattern generator 102 may be a MEMs array, a liquid crystal display, or any other type of display for generating patterns, altering, i.e., reflecting or selectively transmitting, the beam of light generated by light source 100 to generate structured light patterns, and projecting the patterns onto an object of interest.

Detector 104 may include a single camera or a plurality of cameras. In the illustrated example, detector 104 includes a high-speed, low-resolution depth extraction camera 106 for detecting reflected structured light patterns and a low-speed, high-resolution color camera 108 for obtaining color images of an object of interest. For real-time structured light depth extraction applications for endoscopic surgery, depth extraction camera 106 may have a frame rate ranging from about 60 frames per second to about 260 frames per second and a resolution of about 640×480 pixels and is preferably tuned to the wavelength of light source 100. Color camera 108 may have a frame rate of no more than about 30 frames per second with a resolution of about 1000×1000 pixels and is preferably capable of detecting reflected light over a broad frequency band.

Light sources 100 and 111 and cameras 106 and 108 may be operated synchronously or asynchronously with respect to each other. In an asynchronous mode of operation, structured light depth extraction and broadband illumination may occur simultaneously. In this mode of operation, a filter corresponding to the frequency band of light source 100 is preferably placed in front of light source 111 or in front of camera 108 to reduce reflected light energy in the frequency band of light source 100. In a synchronous mode of operation, light source 100 may be turned off during broadband illumination of the object by light source 111. In this mode of operation, since there should be no excess energy caused by light source 100 that would adversely affect the detection of broadband light, the bandpass or notch filter in front of light source 111 or camera 108 may be omitted.

Separating the depth extraction and broadband light detection functions using separate cameras optimized for their particular tasks decreases the data storage and processing requirements of downstream devices. However, the present invention is not limited to using separate cameras for depth extraction and broadband light detection. In an alternate embodiment, a single camera may be used for both real time structured light depth extraction and broadband light detection without departing from the scope of the invention. Such a camera preferably has sufficient resolution for broadband light detection and sufficient speed for real-time structured light depth extraction.

Real-time depth extraction engine/controller 110 may be a general-purpose computer, such as a personal computer, with appropriate video processing hardware and depth extraction software. In one exemplary implementation, real-time depth extraction engine/controller 110 may utilize a Matrox Genesis digital signal processing board to gather and process images. In such an implementation, real-time depth extraction software that determines depth based on transmitted and reflected images may be implemented using the Matrox Imaging Library as an interface to the digital signal processing board.

In an alternate implementation, the specialized digital signal processing board may be replaced by a frame grabber and processing may be performed by one or more processors resident on the general purpose computing device. Using a frame grabber rather than a specialized digital signal processing board reduces the overall cost of the real-time structured light depth extraction system over conventional systems that utilize specialized digital signal processing boards. In yet another exemplary implementation, depth extraction engine/controller 110 may distribute the processing for real-time depth calculation across multiple processors located on separate general purpose computing platforms connected via a local area network. Any suitable method for distributed or single-processor-based real-time structured light depth extraction processing is intended to be within the scope of the invention.

In FIG. 1, the system also includes imaging optics for communicating light from laser 100 to pattern generator 102. In the illustrated example, the optics include a linear polarizer 112 and expansion optics 114 and 116. Linear polarizer 112 linearly polarizes light output from laser 100. Linear polarization 112 is desired for imaging surfaces within a patient's body to reduce specularity. Expansion optics 114 and 116 may include a negative focal length lens spaced from pattern generator 102 such that the beam width of the beam that contacts pattern generator 102 is equal to the area of pattern generator 102 used to generate the patterns. A collimator may be optionally included between light source 100 and pattern generator 102. Using a collimator may be desirable when laser light source 100 comprises a bare laser diode. The collimator may be omitted when laser light source 100 is physically structured to output a collimated beam of light.

In order to illuminate objects 118 in interior region 120 of a patient's body, the depth extraction hardware illustrated in FIG. 1 is coupled to the interior of a patient's body via an endoscope 122. Endoscope 122 may be a laparoscope including a first optical path 124 for transmitting structured light patterns into a patient's body and a second optical path 126 for communicating reflected structured light patterns from the patient's body. In order to fit the patterns within optical path 124, the system illustrated in FIG. 1 may include reduction optics 128 and 130. Reduction optics 128 and 130 may include a positive focal length lens spaced from the aperture of endoscope 122 such that the beamwidth of the structured light entering endoscope 122 is less than or equal to the diameter of optical path 124. In experiments, it was determined that even when the images reflected from pattern generator 102 are compressed, due to the collimated nature of light emanating from laser 100, little distortion is present in the images. As a result, depth information can be extracted more quickly and accurately.

Figure 2A:
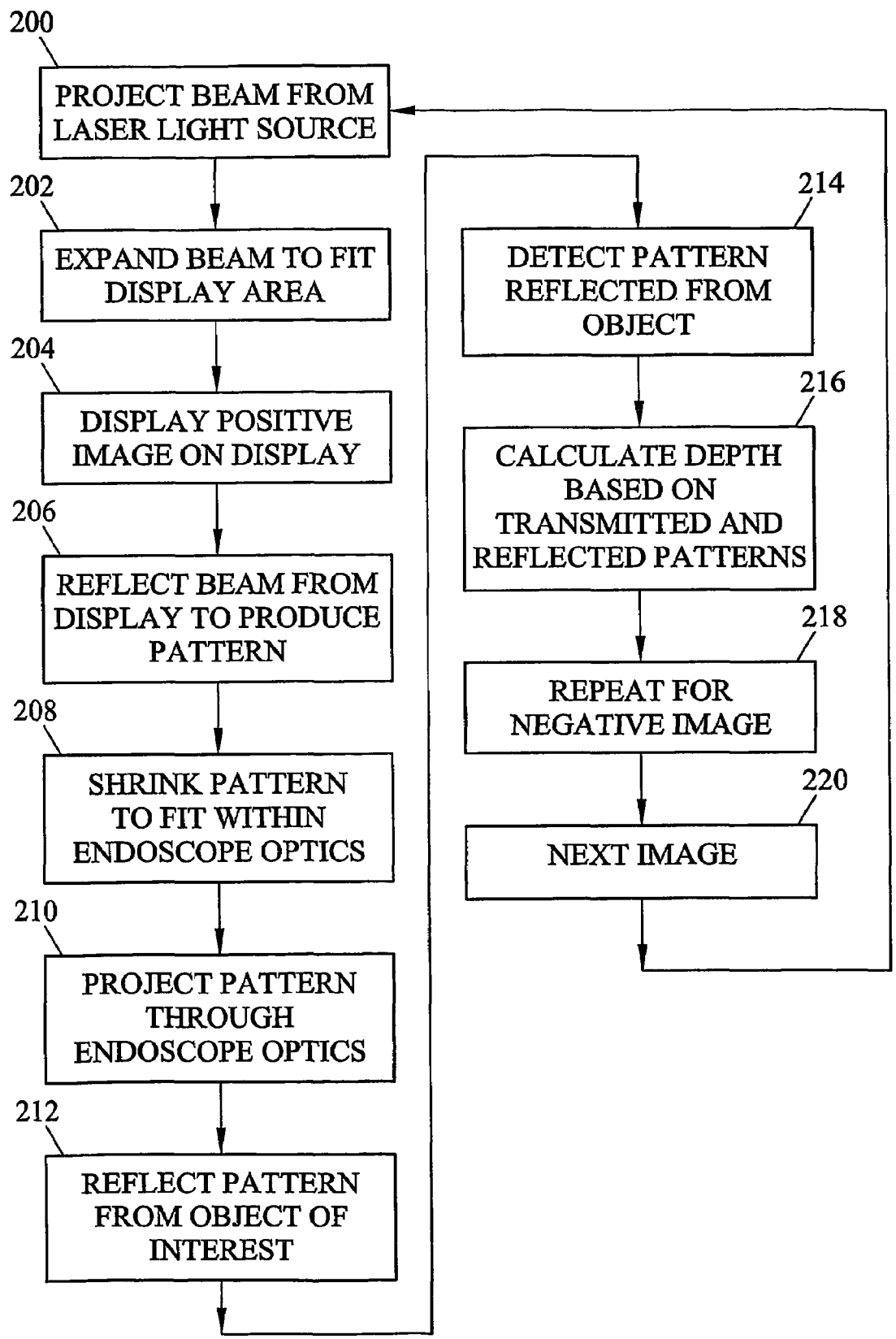
FIG. 2A is a flow chart illustrating exemplary steps for operating the system illustrated in FIG. 1 to perform laser-based real-time structured light depth extraction according to an embodiment of the invention.

FIG. 2A is a flow chart illustrating exemplary steps for performing laser-based real-time structured light depth extraction in an endoscopic surgical environment using the system illustrated in FIG. 1. Referring to FIG. 2A, in step 200, real-time depth extraction engine/controller 110 controls light source 100 to project a beam of laser light. The beam of laser light is preferably collimated. In step 202, beam expansion optics expand the beam to fit the area of display 102 where patterns are projected. In step 204, real-time depth extraction engine/controller controls display 102 to display an image. It was determined that for ferro-reflective displays, the frame rate of the display can be doubled by displaying a positive image followed by a negative image. In other words, every pixel that is on in the first image is off in the second image and vice versa. Accordingly, in step 202, display 102 displays the positive image.

The present invention is not limited to displaying positive and negative images on a ferro-reflective display. Any sequence of images suitable for real-time structured light depth extraction is intended to be within the scope of the invention. In one implementation, real-time depth extraction engines/controller 110 may adaptively change images displayed by display 102 to extract varying degrees of depth detail in an object. For example, for higher resolution, real-time depth extraction engine/controller 110 may control display 102 to display images with narrower stripes. In addition, within the same image, a portion of the image may have wide stripes and another portion may have narrow stripes or other patterns to extract varying degrees of detail within the image.

The resolution of the depth detail extracted may be controlled manually by the user or automatically by real-time depth extraction engine/controller 110. For example, in an automatic control method, real-time depth extraction engine/controller 110 may automatically adjust the level of detail if depth calculation values for a given image fail to result in a depth variation that is above or below a predetermined tolerance range, indicating that a change in the level of depth detail is needed. In a manual control method, the user may change the level of detail, for example, by actuating a mechanical or software control that triggers real-time depth extraction engine/controller 110 to alter the patterns and increase or decrease the level of depth detail.

In step 206, display 102 reflects the beam of light from laser 100 to produce a structured light pattern. In step 208, beam compression optics 128 and 130 shrink the pattern to fit within optical path 124 of endoscope 122. In step 210, the pattern is projected through the endoscope optics. In step 212, the pattern is reflected from object 118 within the patient's body. The reflected pattern travels through optical path 126 of endoscope 122. In step 214, high speed camera 106 detects the reflected pattern and communicates the reflected pattern to real-time depth extraction engine/controller 110.

In step 216, real-time depth extraction engine/controller 110 calculates depth based on the transmitted and reflected patterns and the positions of camera 106 and display 102 as projected through the optics of endoscope 122. For example, the depth value may indicate the distance from object 118 to the end of endoscope 122. An exemplary algorithm for classifying pixels and calculating depth will be described in detail below.

As stated above, if a ferro-reflective display is used, a negative image may be projected after display of a positive image. Accordingly, in step 218, steps 202-216 are repeated and depth values are calculated for the negative image. In an alternate implementation of the invention, pattern generator 102 may generate only positive images.

In step 220, real-time depth extraction engine/controller 110 generates a new image and steps 200-218 are repeated for the new image. The new image may be the same as or different from the previous image. The process steps illustrated in FIG. 2 are preferably repeated continuously during endoscopic surgery so that real-time depth information is continuously generated. The depth information may be used to generate a synthetic 3-D image of object 118. The synthetic image may be combined with a real image and displayed to the surgeon.

Figure 2B:
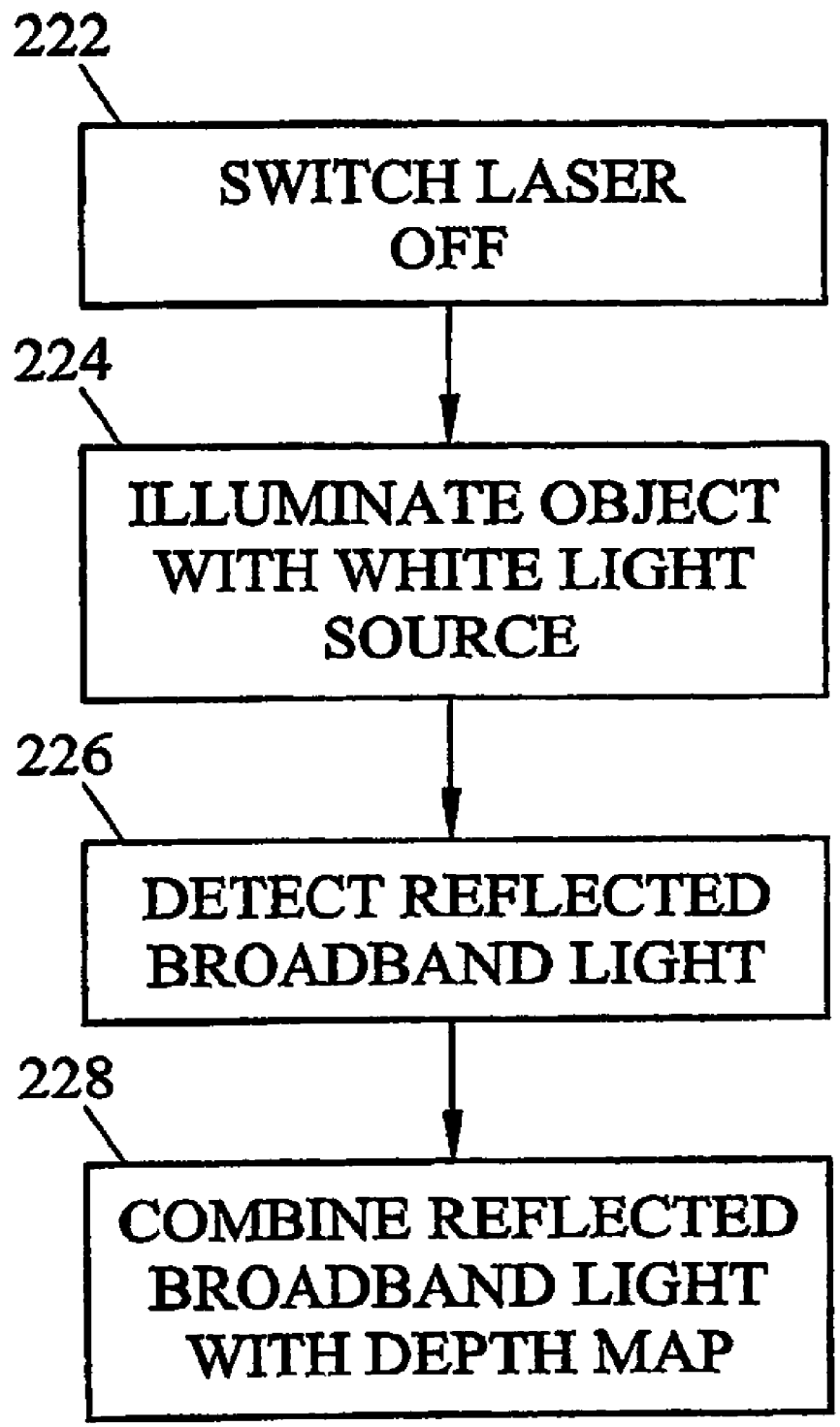
FIG. 2B is a flow chart illustrating exemplary steps for broadband illumination of an object and generating color images of the object according to an embodiment of the present invention.

FIG. 2B illustrates exemplary steps that may be performed in generating color images. The steps illustrated in FIG. 2B may be performed concurrently with steps 202-216 in FIG. 2A. For example, referring to FIG. 2B, step 222 may be performed after laser 100 is turned on to illuminate display 102. Once a pulse of light has been generated, laser 100 may be switched off so that broadband illumination of object 118 can occur. As stated above, switching between laser and broadband illumination is referred to herein as the synchronous mode of operation. Alternatively, laser 100 may be continuously on while broadband illumination occurs. This mode of operation is referred to herein as the asynchronous mode of operation. In step 224, real-time depth extraction engine/controller 110 illuminates object 118 using broadband light source 111. Broadband light source 111 generates a beam of white light that may be communicated through a separate optical path in endoscope 122 from the path used for laser light. For example, endoscope 122 may include a fiber optic bundle for communicating the broadband light to the interior of a patient's body. The reflected white light may be communicated through path 126 in endoscope 122 or through the same optical path as the transmitted light. In step 226, high-resolution camera 108 detects the broadband light reflected from the object. In step 228, real-time depth extraction engine/controller 110 combines the reflected broadband light with the depth map generated using the steps illustrated in FIG. 2A to produce a 3-dimensional color image of object 118.

Figure 3:
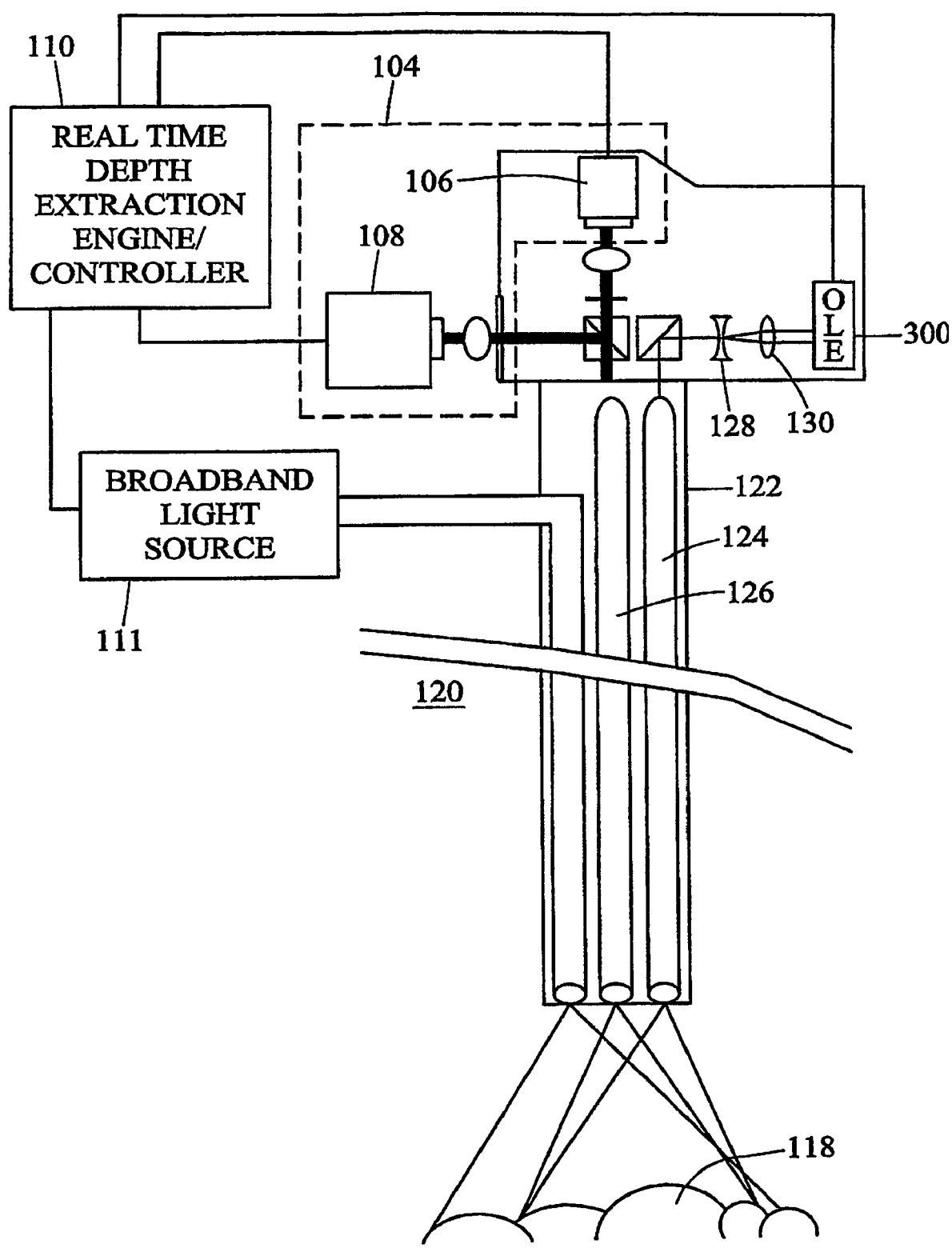
FIG. 3 is a schematic diagram of a laser-based real-time structured light depth extraction system according to an alternate embodiment of the present invention.

FIG. 3 illustrates a real-time structured light depth extraction system according to an alternate embodiment of the present invention. As stated above, in one exemplary implementation, light source 100 and display 102 may be replaced by a self-illuminating display, such as an organic light emitting (OLE) display. In an OLE display, organic polymers replace conventional semiconductor layers in each light-emitting element. OLE displays have sufficient brightness to be self-illuminating and may be suitable for an endoscopic surgical environment. In FIG. 3, OLE display 300 replaces reflective display 102 and laser light source 100 illustrated in FIG. 1. OLE display is preferably configurable to emit narrowband light, as discussed above with regard to laser light source 100. The frequency range of light emitted by display 300 may be in the visible or non-visible range. For human and animal surgical environments, OLE display 300 is preferably capable of emitting green light. Detector 106 is preferably tuned to the frequency band being projected by OLE display 300.

Using OLE display 300 eliminates the need for beam expansion optics 114 and 116. Beam compression optics 128 and 130 may be still be used to compress the size of the image to fit within optical path 124 of endoscope 122. Alternatively, OLE display 300 may be configured to produce a sufficiently small image to fit within the diameter of optical path 124. In such an implementation, beam compression optics 128 and 130 may be omitted. Thus, using an OLE display may reduce the number of components in a real-time structured light depth extraction system for endoscopic surgery according to an embodiment of the present invention.

Figure 4:
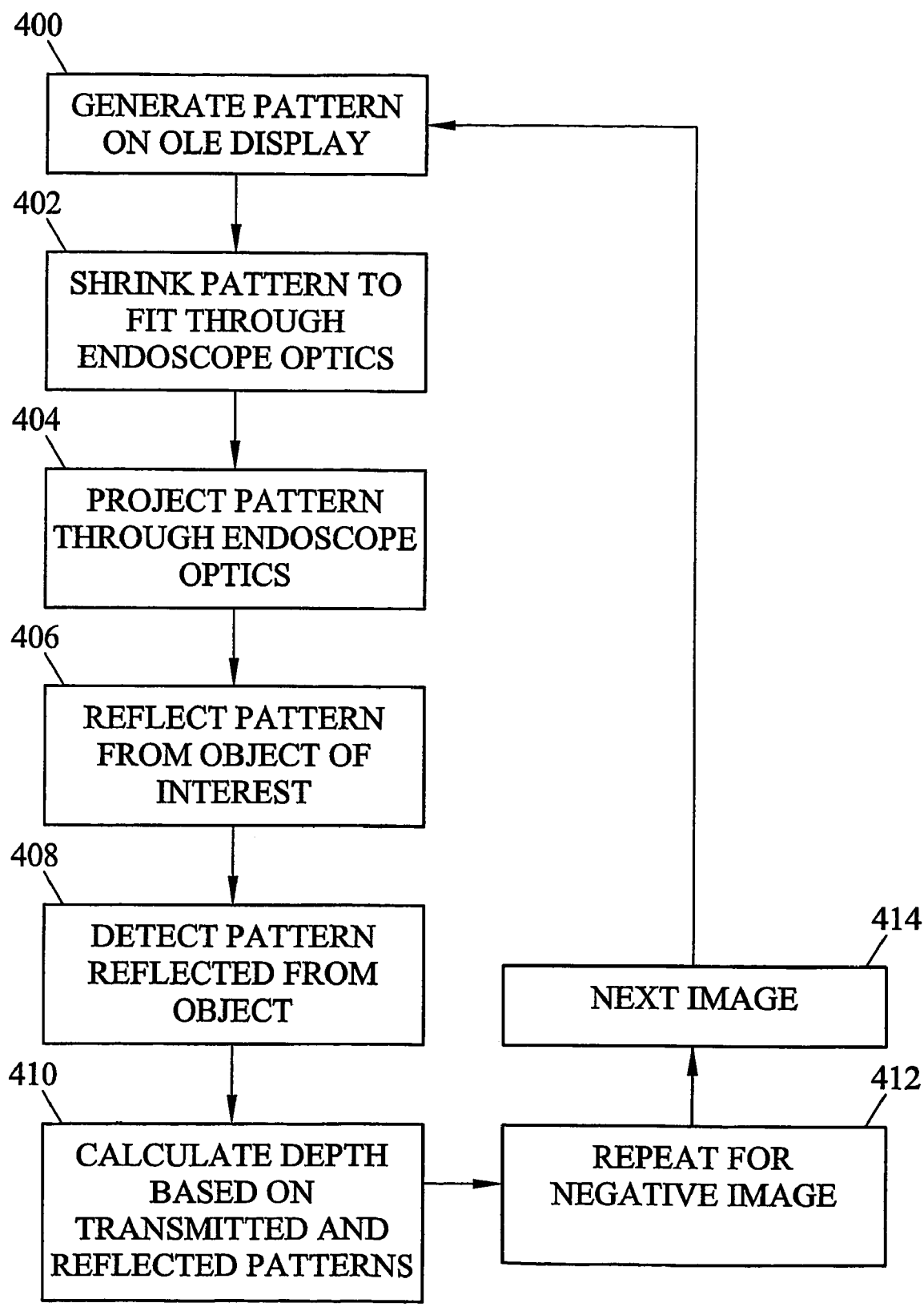
FIG. 4 is a flow chart illustrating exemplary steps for operating the system illustrated in FIG. 3 to perform real-time structured light depth extraction in an endoscopic surgical environment according to an embodiment of the invention.

FIG. 4 is a flow chart illustrating exemplary steps for performing real time structured light depth extraction in an endoscopic surgical environment using the system illustrated in FIG. 3. Referring to FIG. 4, in step 400, real-time structured light depth extraction engine/controller 110 controls OLE display 300 to generate a structured light pattern. In step 402, beam compression optics 128 and 130 compress the pattern to fit within optical path 124 of endoscope 122. In step 404, the pattern is projected through optical path 124 and into the patient's body. In step 406, the pattern is reflected from object 118. The reflected pattern travels through optical path 126 in endoscope 122. In step 408, the reflective pattern is detected by high-speed camera 106. In step 410, real-time depth extraction engine/controller 110 calculates depth based on the transmitted and reflected pattern.

If a performance advantage can be achieved by displaying sequences of positive and negative images, display 300 may be controlled to display a negative image after each positive image. Accordingly, in step 412, steps 400-410 are repeated for the negative image. In step 414, real-time depth extraction engine/controller generates a new image that is preferably different from the original image. Steps 400-412 are then repeated for the new image. The steps illustrated in FIG. 2B for broadband illumination and color image generation may be performed concurrently with the steps illustrated in FIG. 400 to produce a color image that is combined with the depth image. The only difference being that in step 200, the OLE display, rather than the laser, may be turned off during broadband illumination. In addition, as discussed above with regard to laser-illumination, detection of structured light patterns and detection of reflected broadband illumination for OLE display illumination may be performed synchronously or asynchronously. Thus, using the steps illustrated in FIG. 4B, an OLE display may be used to perform real-time structured light depth extraction in an endoscopic surgical environment.

Structured Light Triangulation Methods

The term "structured light" is often used to specifically refer to structured light triangulation methods, but there are other structured light methods. These include the depth from defocus method. Laser scanning methods are distinct from structural light methods because laser scanning methods scan a single point of light across an object. Scanning a point of light across an object requires more time than the structured light methods of the present invention which simultaneously project a plurality of pixels of laser light onto the object being imaged. As stated above, the present invention may utilize multiple stripes of varying thickness to extract depth with varying resolution. The mathematics of calculating depth in depth-from-stereo or structured light triangulation methods will be described in detail below. Any of the structured light triangulation methods described below may be used by real-time depth extraction engine/controller 110 to calculate depth information in real time.

Structured light is a widely used technique that may be useful in endoscopic surgical environments because it:

Works on curved surfaces

Works independent of surface texture

Can work with some specular components in the scene

Structured light methods usually make some assumptions about how much variation in surface properties can be present in the scene. If this tolerance is exceeded, the method may not be able to recover the structure from the scene and may fail.

Light structures can be any pattern that is readily (and ideally unambiguously) recovered from the scene. The difference between the pattern injected into the scene and the pattern recovered gives rise to the depth information. Stripe patterns are frequently used because of the easy way that they can be recognized and because of some mathematical advantages discussed below. Many methods have been proposed to distinguish projected stripes from one another. These include color coding, pattern encoding (like barcodes for each stripe), and temporal encoding. Color coding schemes rely on the ability of the projector to accurately produce the correct color, the surface to reflect back the correct color, and the camera to record the correct color. While projectors and cameras can be color calibrated, this puts serious constraints on the appearance and reflective properties of objects to be scanned. Pattern encoding schemes assume enough spatial coherence of the object being scanned. Pattern encoding schemes assume enough spatial coherence of the object being scanned that enough of the code can be found to identify a stripe. Temporal encoding of stripe patterns is very popular because it makes few assumptions about the characteristics of the surface, including possibly working with surface texture. Motion during the scanning sequence can be a significant problem.

A simple and effective way to temporally encode many stripes is to project multiple patterns into the scene and use a binary encoding for each stripe. Assuming no movement of the scene or the scanner, the stripe that each pixel of the image belongs to is encoded by whether or not the pixel in each image is illuminated or not. This method reduces the number of projected patterns needed to encode n stripes to $\log_2 n$. A variety of sequences have been developed to reduce the potential for error by misidentification of a pixel's status in one or more images.

Several systems use the position of the edge of stripes rather than the position of the stripe itself for triangulation. One of the advantages to doing this is that subpixel accuracy for this position can be achieved. Another advantage of this method is that the edges may be easier to find in images with variations in texture than the stripes themselves. If the reflective properties of the anticipated scene are relatively uniform, the point of intersection of a plot of intensity values with a preset threshold, either in intensity value or in the first derivative of intensity, can be sufficient to find edges with subpixel precision. If a wider range of reflective patterns are anticipated, structure patterns can be designed to ensure that, in addition to labeling pixels as to which stripe they belong, each of these edges is seen in two images but with the opposite transition (that is, the transition from stripe one to two is on-off in one image and off-on in a later image). The point where a plot of intensity values at this edge cross each other can be used as a subpixel measure of the position.

The real-time system developed by Rustinkiewicz and Hall-Hot uses edges in an even more clever way. They recognized that a stripe must be bounded by two stripes and, over a sequence of our projected patterns, the status of both stripes can be changed arbitrarily. This means that 256 ($2^{2^4}$) different coding sequences can be projected over the sequence of four frames. After removing sequences in which the edge cannot be found (because the neighboring stripes are "on-on" or "off-off") in two sequential frames and where a stripe remains "on" or "off" for the entire sequence, the latter sequence is removed to avoid the possible confusion of their edge-finding method of these stripes with texture on the surface of the object. After such considerations, one hundred ten (110) stripe edge encodings may be used. This method could potentially be applied using more neighboring stripes to encode a particular stripe edge or a larger number of frames. For n frames and m stripes to encode each boundary the number of possible stripes that can be encoded is approximately proportional to $(m^2)^n$. It should be noted that to project x stripe patterns, O(logx) frames are needed as in the case of binary encoded stripes except the scaler multipliers on this limiting function are generally much smaller for this technique as compared to binary encoding.

The Rustinkiewicz triangulation system uses the rate of change (first derivative) of intensity to find boundary edges with the sign determining what type of transition is observed. Efficient encoding demands that many edges be encoded by sequences in which the edge is not visible in every frame. The existence and approximate position of these "ghost" edges is inferred and matched to the nearest found edge or hypothesized edge in the previous frame. The encoding scheme limits the number of frames in which an edge can exist as a ghost, but the matching process limits the motion of objects in the scene to not more than half of the average stripe width between frames. The Rustinkiewicz triangulation system may have a lower threshold for motion if objects have high-frequency textures or any sudden changes in surface texture that would be misinterpreted as an edge. The Rustinkiewicz triangulation method might also fail for objects that are moving in or out of shadows (that is, the camera sees a point on the surface, but the projector cannot illuminate it). The primary application for this system is building high-resolution three-dimensional models of objects. A modified iterated closest point (ICP) algorithm is used to match and register the range images acquired from frame to frame in order to build up the dataset.

The speed of structured light triangulation systems is limited by three major factors. These are the rate at which structured patterns can be projected, the rate at which an image of the scene with the structured pattern present can be captured, and the rate at which the captured images can be processed. The method of Rusinkiewicz reduces the demands on the projector and camera by use of sophisticated processing and judicious use of assumptions of spatial and temporal coherence. An alternative approach that may be used with implementations of the present invention is to use simple, high-speed, hardware acceleratable algorithms, while placing greater demands on the camera and projector portion of the system both to compensate for motion and to achieve a useful rate of output for an augmented reality visualation system for endoscopic surgery.

Many currently available displays including LCD and micro-electromechanical systems (MEMS) (e.g. Texas Instruments' DMD™ digital micromirror display) based devices are used to project images with refresh rates over 60 Hz. These devices are frequently used to project color imagery by using small time slices to project component colors of the total displayed imagery. The underlying display in these devices is capable of projecting monochrome images (black and white, not grayscale) at over 40 kHz (for a DMD based device). High-speed digital cameras are available that capture images at over 10 kHz. While cameras are advertised that capture at these extremely high rates, most cannot capture "full frame" images at the rate. Currently advertised cameras can record sequences at 1 kHz with a resolution equivalent to standard video (640×480, non-interlaced). While most of these devices are simply used for recording short high-speed sequences, image capture and analysis cards are available which are capable of handling the data stream and performing simple analysis at high data rates.

Given the devices that are currently available, the remaining challenges include the development of algorithms that can be executed at high speed, algorithms that can deal with texture or the absence of texture, specularity, and small amounts of motion. An additional challenge is to build a device that satisfies these conditions and is compatible with laparoscopic surgery. Exemplary algorithms for recovering depth in a laparoscopic surgical environment will now be described.

Mathematical Model for Recovering Depth

A structured light depth extraction method suitable for use with the present invention can be thought of as a special case of obtaining depth from stereo. Instead of a second camera, a projector is used so that disparity can be defined as the difference between where the projector puts a feature and where the camera finds the feature (rather than being the difference between where the two cameras find a scene feature). First, a simple mathematical model of depth from stereo will be discussed, then the changes needed to apply this model to a camera and projector will be discussed.

Depth from Stereo

Figure 5:
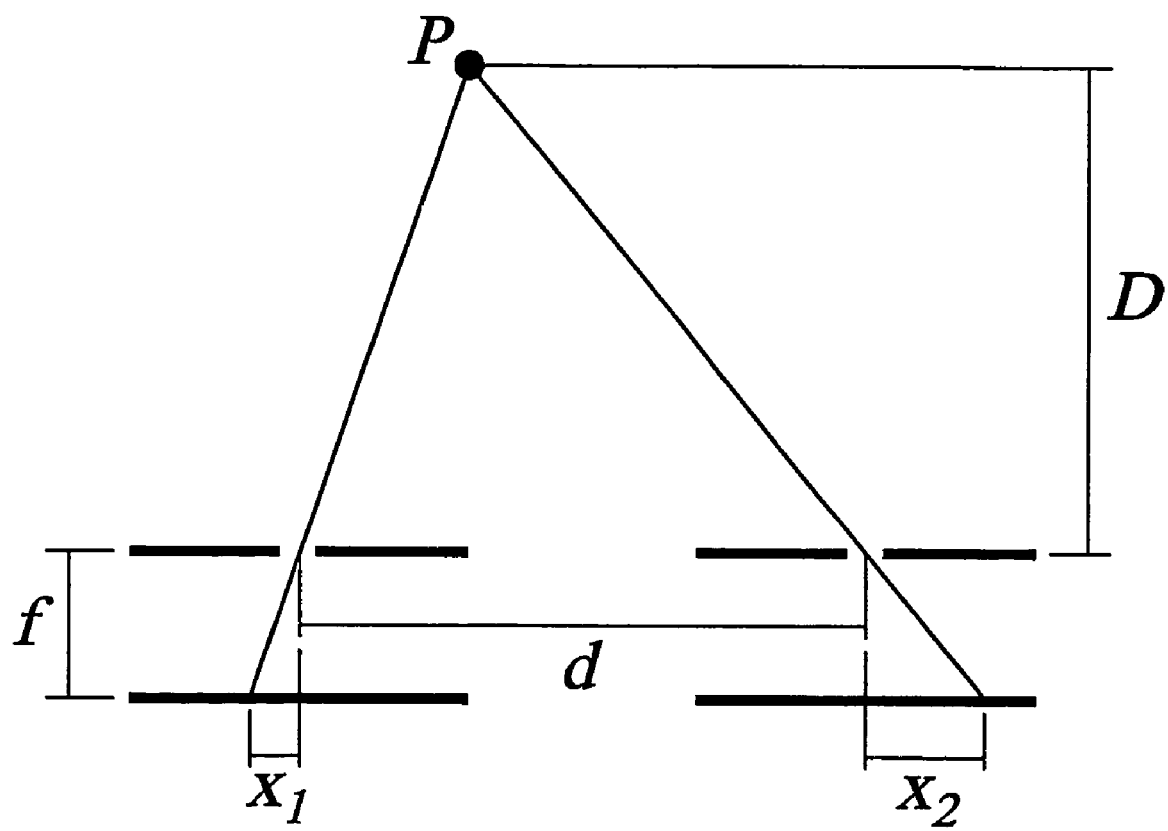
FIG. 5 is a schematic diagram illustrating a triangulation method for determining depth using two one-dimensional cameras suitable for use with embodiments of the present invention.

A schematic diagram of a single scan line depth from stereo depth extraction system is shown in FIG. 5. In such a simple case of depth from stereo, the cameras are coplanar, are directed parallel to each other, and are ideal "pin-hole" cameras with identical internal parameters. In FIG. 5, the thick lines represent the cameras, P is the point in space observed, d is the separation between the cameras, D is the distance to P, f is the distance between the pinhole and the imaging plane of the cameras, and $x_1$ and $x_2$ are the position of the observed object on the imaging plane of the two cameras.

In this case, the relationship between the depth of a point seen by both cameras (D), focal distance (f), camera separation (d), and the observed position of the point on the image planes of both cameras ($x_1$ and $x_2$) is (by similar triangles):

$$D = \frac{df}{x_1 - x_2} \quad (1)$$

In Equation (1), the denominator contains the term $x_1$ and $x_2$, which is the disparity or difference of position of the object in the two cameras.

This relationship holds if the cameras have two-dimensional imagers rather than the one-dimensional imagers that were initially assumed. This can be demonstrated by observing that the angle of elevation between the ray starting at the pinhole and ending at the point in space (φ) is the same if the earlier assumptions about the cameras are maintained. The implication of this observation is that if the point is observed at a position ($x_1$, $y_1$) in the first camera, its position in the second camera must be at ($x_2$, $y_1$)—that is, its position in the second camera is limited to a single horizontal line. If some a priori information is known about the distance to the point, the portion of the image can be further reduced.

Figure 6:
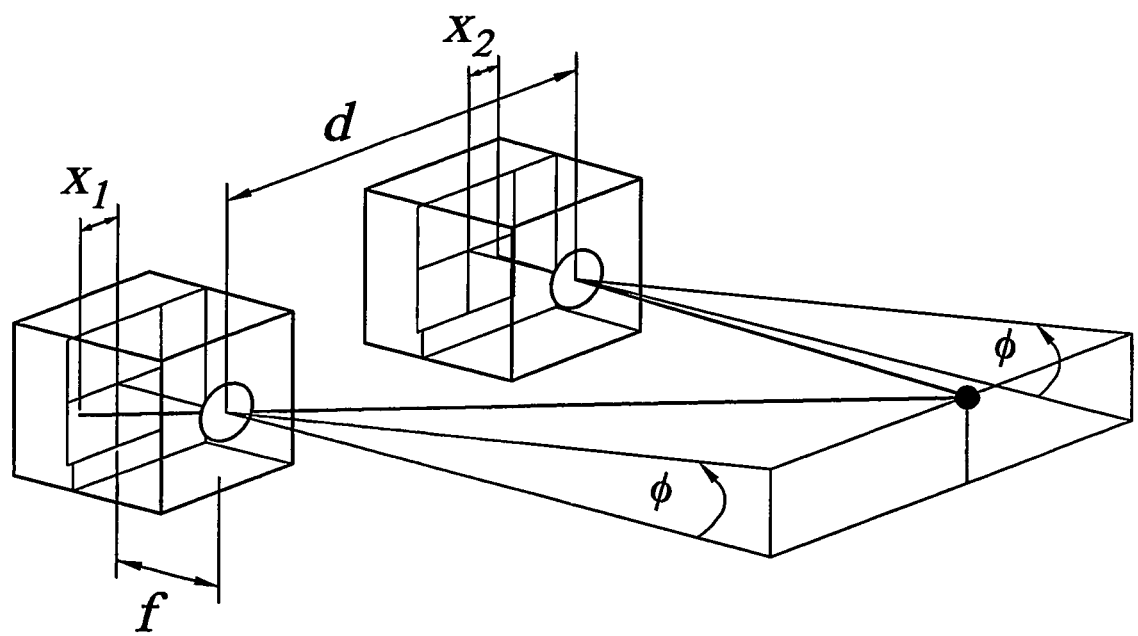
FIG. 6 is a schematic diagram illustrating a triangulation method for determining depth using two two-dimensional cameras suitable for use with embodiments of the present invention.

FIG. 6 shows a schematic diagram of two two-dimensional pinhole cameras observing a point in space. In FIG. 6, the cubes represent the cameras, d is the separation between the cameras, D is the distance to the observed point, f is the distance between the pinhole and the imaging plane of the cameras, and $x_1$ and $x_2$ are the position of the observed object on the imaging plane of the two cameras. The angle of elevation, φ, must be identical in the two cameras.

As the initial assumptions are broken, the relationship becomes more complicated. Fortunately, points projected onto a two-dimensional plane can be reprojected onto a different plane using the same center of projection. Such a reprojection can be done in two or three-dimensional homogenous coordinates and takes the following form:

$$\begin{bmatrix} x_r \\ y_r \\ \omega \end{bmatrix} = \begin{bmatrix} c_{11} & c_{12} & c_{13} \\ c_{21} & c_{22} & c_{23} \\ c_{31} & c_{32} & c_{33} \end{bmatrix} \begin{bmatrix} x \\ y \\ 1 \end{bmatrix} \quad (2)$$

Since this a projection in homogenous coordinates, the correct coordinates on the reprojected plane ($x_c$, $y_c$) will then be:

$$\begin{bmatrix} x_r \\ y_r \end{bmatrix} = \begin{bmatrix} \frac{x_c}{\omega} \\ \frac{y_c}{\omega} \end{bmatrix} \quad (3)$$

Reprojection of this type is performed very efficiently by current graphics and image processing hardware. In the special case where reprojection is done onto parallel planes, ω becomes a constant for all coordinates (x, y) in the original image. An important implication is the observation that, because the operation of perspective projection preserves straight lines as straight lines in the resulting image, an object observed in a particular location in one camera's view must be located somewhere along a straight line (not necessarily on a scan line) in the other camera's image. This constraint is known as the epipolar constraint.

Further simplification can be achieved if reprojection is done to planes that are nearly parallel. This assumes that the original planes of projection are very similar to the rectified ones. That is, the center of projections are approximately aligned. In this case, ω varies little in the region being reprojected. Therefore, rough approximation of the depth calculation, without using any reprojection, is simply (where $C_n$, k, and K are appropriately selected arbitrary constants):

$$D = \frac{K}{C_1 x_1 + x_2 + C_2 y_1 + C_3 y_2 + C_4} \quad (4)$$

The approximation in Equation (4) can be used as the basis of a simple calibration for a structured light depth extraction system. As it is a rough approximation, it should be applied with great caution if a high degree of accuracy is needed.

The process of rectification can also be used to correct for distortion of camera images from an idealized pin-hole model. There are a variety of methods to measure the distortion in camera images. These methods use graphics or image processing hardware to rapidly correct for these distortions to create a distortion-free image. While rectification, particularly the reprojection in homogeneous coordinates can be done in hardware, it is not always advisable to do so. Practical implementation of reprojection usually entails a loss in image quality. Minor corrections usually cause little loss of information, but large differences in the position of the planes of projection can cause a loss of a large number of pixels in some portions of the resultant image and smearing of pixels across wide areas in other portions of the resultant image. In these cases it is wise to find positions of objects in the original images, and reproves only the found (x, y) coordinates of those objects. In most cases it is easier to correct for camera distortion before looking for objects in the images so that the epipolar constraints are straight lines and not the curved lines that are possible in camera images with distortions.

Depth Extraction Using a Projector and a Camera

When one of the cameras from the model discussed in the previous section is replaced with a projector, the meaning of some of the steps and variables changes. These changes have several important implications.

In a real-time structured light depth extraction system of the present invention, one of the cameras in FIG. 6 may be replaced with a projector that is essentially an inverse of a pinhole camera, like a camera obscura projecting on the wall of a darkened room. The projector by itself gathers no data about the point in space. If a single ray of light is projected into space, and no other light is available, then the second camera can now unambiguously see the point where that ray strikes a distant surface. In this situation, the coordinate of the light being projected is $x_1$ and the point where the camera sees that point of light is $x_2$. If two-dimensional cameras and projectors are used, the ray $(x_1, y_1)$ is illuminated by the projector, illuminating the surface at a point which is then seen by the camera at the point $(x_2, y_2)$. The mathematical relationships of the previous section then hold.

Reprojection and rectification, as described in the previous section, take on a new meaning for the projector. Rather than "undistorting" an acquired image, the projected image can be "predistorted" to account for the projection optics and variations in the position, orientation, and characteristics of the relative position of the camera and projector combination. This predistortion should be the inverse of the undistortion that would need to be applied if it were a camera rather than a projector.

Another implication of the epipolar constraints in the case of the projector-camera combination is that more than one ray can be illuminated simultaneously and they can easily be distinguished. In the simplest case, where the camera and projector have identical internal characteristics, are pointed in a parallel direction, and have coplanar planes of projection, the epipolar lines run parallel to the x axis. A ray projected to $(x_1, y_1)$ will only be seen along the $y_1$ scanline in the camera. A second ray projected through $(x_2, y_2)$ will only possibly be seen on the $y_2$ scanline in the camera. In practice it is usually simplest to project vertical stripes (assuming that the camera and projector are horizontally arranged). Because each scanline in the camera corresponds to a single horizontal line in the camera, the found x position of the stripe projected through position $x_s$ can be converted to depth using Equation (1), after appropriately substituting $x_s$:

$$D = \frac{df}{x_s - x} \quad (5)$$

Image Processing

As stated above, in order to perform real-time structured light depth extraction, it is necessary to locate or classify pixels or stripes from the transmitted image in the reflected image so that offsets can be determined. The following is an example of a method for classifying pixels in a real-time structured light depth extraction system suitable for use with embodiments of the present invention. In the example, the following source data is used:

m images, P, with projected stripe patterns m images, N, with the inverse stripe patters projected m is the number of bits of striping (for binary encoded structured light)

Non-Optimized Method

One sub-optimal method for classifying pixels includes the following steps:

1) Subtract the nth negative image, $N_n$, from the nth positive image, $P_n$.

$$C_n = P_n - N_n \quad (6)$$

2) Label each pixel that belongs to an 'off' stripe as 0, as 1 for an 'on' stripe, and leave pixels that cannot be identified unmarked. The 'on' stripes can be identified because their intensity values in the difference image $C_n$ will be greater than a threshold level γ, while 'off' pixels will have an intensity level less the −γ. Pixels with intensity values between γ and −γ cannot be identified (as in the case of shadows, specular reflections, or low signal-to-noise ratio).

$$L_n = \begin{cases} 0 & \text{if} & C_n \leq 2^{b-1} - \gamma \\ 1 & \text{if} & C_n \geq 2^{b-1} + \gamma \\ \text{undefined} & \text{if} & 2^{b-1} - r < C_n < 2^{b-1} + \gamma \end{cases} \quad (7)$$

3) Record which pixels cannot be identified in this image pair.

$$U_n = \begin{cases} 0 & \text{if} & 2^{b-1} - r < C_n < 2^{b-1} + \gamma \\ 1 & \text{otherwise} \end{cases} \quad (8)$$

In the case of binary encoding of the stripes, an image with each pixel labeled with the stripe encoded, S can be created by $$S = \left(1 + \sum_{i=1}^{m} 2^i L_i\right) \prod_{i=1}^{m} U_i \quad (9)$$

The multiplication by the product of all images $U_n$ ensures that any pixel in which the stripe pattern could not be identified in any image pair is not labeled as belonging to a stripe. Thus, the image S contains stripes labeled from 1 to $2^m+1$ with zero value pixels indicating that a stripe could not be identified for that pixel in one or more image pairs.

Optimized Method

Equation (6) is approximately normalized so the result fits into the image data type (b bits). This will most likely result in the loss of the low order bit.

$$C(n) = \frac{P_n}{2} + 2^{b-1} - \frac{N_n}{2} \quad (10)$$

The next step is to apply thresholds to identify and mark the 'on' and 'off' pixels. First, threshold to find the 'on' pixels by setting bit n−1 if the intensity of that pixel is greater than 128 plus a preset level γ. Next, threshold 'off' pixels by setting bit n−1 to zero for pixels with intensity greater than 128 minus a preset level γ. Pixels that are not part of these two ranges are labeled non-identifiable $$L(n) = \begin{cases} 0 & \text{if} & C(n) \leq 2^{b-1} - \gamma \\ 2^{n-1} & \text{if} & C(n) \geq 2^{b-1} + \gamma \\ 2^m & \text{if} & 2^{b-1} - \gamma < C(n) < 2^{b-1} + \gamma \end{cases} \quad (11)$$

by setting the mth bit.

In this way, Equation (11) combines Equations (7) and (8) from the non-optimized version into a single operation. Likewise, two images, $U_n$ and $L_n$, in the non-optimized method can be combined into a single $L_n$.

The set of images L may be combined with a bitwise OR as they are generated or as a separate step creating a stripe encoded image, S.

$$S = \bigcup_{i=1}^{n} L(i) \quad (12)$$

The resulting image S from the optimized method differs from that obtained in the non-optimized method in that non-identified pixels have values greater than $2^m$ rather than having a value of 0.

The stripe labeled image S may be converted to a range image using normal techniques used in structured light as discussed above. Pre-calibrated look-up tables and regression fitted functions may be useful methods to rapidly progress from segmented images to renderable surfaces.

Performance

Table 1 below shows the time to complete the image processing phase in a prototype real-time structured light depth extraction system. This implementation is capable of finding stripes for 7-bits of stripe patterns at a rate of ten times per second. Significant optimizations still remain that result in much faster operation. One exemplary implementation uses the Matrox Imaging Library (MIL) as a high-level programming interface with the Matrox Genesis digital signal processing board. Using MIL greatly simplifies programming the digital signal processors but adds overhead and loss of fine level tuning. Additionally, image processing commands through MIL are issued to the Genesis board via the system bus while low level programming of the processors allow the processors to run autonomously from the rest of the PC. Other processes on the PC cause delays up to 50 milliseconds.

TABLE 1

Depth Extraction Performance

|  | Convolution | n = 7 | n = 5 | n = 3 |
|---|---|---|---|---|
| Camera | ON | 100 ms | 73 ms | 47 ms |
| capture off | OFF | 88 ms | 64 ms | 41 ms |
| Camera | ON | 2203 ms | 1602 ms | 967 ms |
| capture on | OFF | 2201 ms | 1568 ms | 966 ms |

Table 1 illustrates performance on a PII/400 MHz with a Matrox Genesis board for capture and processing. Performance is based on the mean time of 20 uninterrupted runs. The value n refers to the number of bits of striping used. For each run, 2n images were processed. Runs performed with camera capture turned off were completed by pre-loading sample images into buffers on the Matrox Genesis card and copying them to new buffers for processing when needed.

When camera capture is enabled, the process is dramatically slowed. A large portion of the time is used for synchronization. Each time a camera capture is needed, the prototype waits at least one and a half frames of video. This is done to ensure that the updated stripe pattern is actually being projected by the projector and to make sure that the camera is at the beginning of the frame when capture starts. Some of these delays can be reduced by triggering the camera only when a capture is needed. In one exemplary implementation, no image processing is performed while waiting for the next images to be captured. A lower level implementation of the system should have the processors on the capture and processing board operate while the next image is being captured.

Results from Prototype

Two experiments were performed on animal tissues to test these methods. The first used a porcine cadaver and an uncalibrated system with off-line processing. The second experiment was performed on chicken organs with on-line segmentation and off-line rendering.

Prototype Calibration and Depth Extraction

Further simplification of Equation 4 is useful to get a reasonable calibration for the prototype system. If the projected patterns and captured images are nearly rectified, then it can be assumed that a scan line in the camera images implies only a single scan line from the projector. Ideally the y terms could all be dropped, but instead the y value from the camera image is maintained:

$$C_2 y_1 + C_3 y_2 = B y_2 + k \qquad (13)$$

This is the assumption that a y position in the first camera implies (linearly) a y position in the second camera. This implies that the original center of projection is very similar (except for scaling) to that used for reprojection (mostly to account for differences in camera characteristics) that might be needed. Equation (13) can be written as $C_2 y_1 + C_3 y_2 + x_2 = B_1 y_2 + B_2 x_2 + k$ as a very rough accommodation for greater variation from the ideal model. While this approach is more correct if one were to measure what the coefficients should be based on camera parameters, the result, Equation (15) is the same for achieving a good fit with a regression model using either model. Under these assumptions $$D = \frac{K}{C_1 x_1 + x_2 + B y_2 + C_4} \qquad (14)$$

Which is equivalent to:

$$\frac{1}{D} = c_1 x_1 + c_2 x_2 + c_3 y_2 + c_4 \qquad (15)$$

Where $c_n$ are appropriate coefficients to fit the model.

A rough calibration of the prototype can then be achieved by linear regression with 1/D as the independent variables, the stripe number, the stripe's position, the scan line in the camera image, and a constant. A linear model also lends itself to rapid calculation on processed images.

The methods and systems described herein may be used to generate depth information in real-time and are particularly well suited for surgical environments, such as endoscopic surgical environments. For example, the methods and systems described herein may be used to generate synthetic images that are projected onto real images of a patient for use in augmented reality visualization systems. One example of an augmented reality visualization system with which embodiments of the present invention may be used as described in commonly-assigned U.S. Pat. No. 6,503,195, the disclosure of which is incorporated herein by reference in its entirety. By using a laser rather than an incandescent lamp, the real-time structured light depth extraction systems of the present invention achieve greater photonic efficiency and consume less power than conventional real-time structured light depth extraction systems. In addition, by separating the structured light image gathering and broadband illumination detection functions, cameras optimized for each function can be used and downstream image processing is reduced.

The present invention is not limited to using laser-based or OLE-display-based depth extraction in an endoscopic surgical environment. The methods and systems used herein may be used to obtain depth in any system in which it is desirable to accurately obtain depth information in real time. For example, the methods and systems described herein may be used to measure depth associated with parts inside of a machine, such as a turbine.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A laser-based real-time structured light depth extraction system comprising:
   (a) a laser light source for producing a collimated beam of laser light;
   (b) a pattern generator being optically coupled to the laser light source for generating a plurality of different structured light patterns, each structured light pattern including a plurality of pixels, wherein each pattern interacts with the collimated beam of laser light to simultaneously project the plurality of pixels onto an object of interest;
   (c) a detector being optically coupled to the object and synchronized with the pattern generator for receiving patterns reflected from the object and for generating signals based on the reflected patterns; and
   (d) a real-time structured light depth extraction engine/controller coupled to the detector and the pattern generator for controlling the projection and detection of the patterns, for calculating, in real-time, depth values for regions of the object based on the signals received from the detector, and for generating and displaying the image of the object based on the calculated depth values, wherein the projection, the calculating, and the generation are repeated continually to update display of the image in real time,
   wherein the three dimensional image of the object comprises a synthetic image and wherein the real time structured light depth extraction engine/controller combines the synthetic image with a real image of a scene and displays the combined image.

2. The system of claim 1 wherein the laser light source comprises a narrowband laser light source.

3. The system of claim 2 wherein the narrowband laser light source comprises a green laser light source.

4. The system of claim 1 wherein the laser light source comprises a laser diode.

5. The system of claim 1 wherein the laser light source is optically coupled to the pattern generator without using a collimator.

6. The system of claim 1 wherein the pattern generator comprises a transmissive pattern generator for selectively passing portions of the collimated beam from the laser to generate the patterns.

7. The system of claim 1 wherein the pattern generator comprises a reflective display for selectively reflecting portions of the collimated beam from the laser to generate the patterns.

8. The system of claim 1 wherein the pattern generator comprises a micro-electromechanical system for interacting with the collimated beam of light to generate the patterns.

9. The system of claim 1 comprising a broadband light source for illuminating the object with broadband light.

10. The system of claim 9 wherein the detector comprises a single camera for detecting the reflected patterns and for detecting broadband light reflected from the object.

11. The system of claim 9 wherein the detector comprises a high-speed, low-resolution camera for detecting the reflected patterns and wherein the system further comprises a low-speed, high-resolution camera for detecting broadband light reflected from the object.

12. The system of claim 11 wherein the cameras and the light sources are operated synchronously with each other such that the laser light source is off when the broadband light source is on for separating depth extraction and broadband illumination functions.

13. The system of claim 11 wherein the cameras and the light sources are operated asynchronously with each other such that the laser light source and the broadband light source are simultaneously on for simultaneous depth extraction and broadband illumination of the object.

14. The system of claim 13 comprising a bandpass filter optically coupled to the broadband light source for reducing power in the frequency band of the laser light source.

15. The system of claim 13 comprising a bandpass filter optically coupled to the high-resolution, low-speed camera for reducing power in the frequency band of the laser light source.

16. The system of claim 11 wherein the high-speed, low-resolution camera is tuned to the bandwidth of the laser light source.

17. The system of claim 1 wherein the real-time structured light depth extraction engine/controller is adapted to control the pattern generator and the detector to project and detect the patterns at a rate of at least about 30 frames per second.

18. The system of claim 1 wherein the real-time structured light depth extraction engine/controller is adapted to control the level of depth detail obtained from the object by changing the patterns generated by the pattern generator.

19. The system of claim 1 comprising an endoscope optically coupled to the pattern generator and the detector for projecting the patterns into the body of a patient and for communicating the reflected patterns from the body of the patient to the detector.

20. The system of claim 19 comprising a beam expander optically coupled to the laser light source and to the pattern generator for expanding light generated from the laser to cover a pattern generated by the pattern generator and a beam compressor optically coupled to the pattern generator and the endoscope for compressing the patterns projected from the pattern generator to fit within an optical path of the endoscope.

21. The system of claim 19 wherein the endoscope comprises a laparoscope.

22. The system of claim 1 wherein the display of the image is updated at a rate of at least about 30 frames per second.

23. A real-time structured light depth extraction system comprising:
(a) a self-illuminating display for generating a plurality of different structured light patterns, each structured light pattern including a plurality of pixels, and for simultaneously projecting the plurality of pixels onto an object of interest;
(b) a detector being optically coupled to the self-illuminating display for receiving patterns reflected from the object and for generating signals based on the reflected patterns; and
(c) a real-time structured light depth extraction engine/controller coupled to the detector and the self-illuminating display for controlling the projection and detection of the patterns and for calculating, in real-time, depth values for regions of the object based on the signals received from the detector.

24. The system of claim 23 wherein the self-illuminating display comprises an organic light emitting (OLE) display.

25. The system of claim 23 comprising a broadband light source for broadband illumination of the object.

26. The system of claim 25 wherein the detector comprises a single camera for detecting the reflected patterns and for detecting broadband light reflected from the object.

27. The system of claim 25 wherein the detector comprises a high-speed, low-resolution camera for detecting the reflected patterns and wherein the system further comprises a low-speed, high-resolution camera for detecting broadband light reflected from the object.

28. The system of claim 27 wherein the cameras, the self-illuminating display, and the broadband light source are operated synchronously with each other such that the self-illuminating display is off when the broadband light source is on for separating depth extraction and broadband illumination functions.

29. The system of claim 27 wherein the cameras, the self-illuminating display, and the broadband light source are operated asynchronously with each other such that the self-illuminating display and the broadband light source are simultaneously on for simultaneous depth extraction and broadband illumination of the object.

30. The system of claim 29 comprising a bandpass filter optically coupled to the broadband light source for reducing power in the frequency band of the self-illuminating display.

31. The system of claim 29 comprising a bandpass filter optically coupled to the high-resolution, low-speed camera for reducing power in the frequency band of the patterns projected by the self-illuminating display.

32. The system of claim 23 wherein the high-speed, low-resolution camera is tuned to the frequency band of the patterns projected by the self-illuminating display.

33. The system of claim 23 wherein the real-time structured light depth extraction engine/controller is adapted to control the pattern generator and the detector to project and detect the patterns at a rate of at least about 30 frames per second.

34. The system of claim 23 wherein the real-time structured light depth extraction engine/controller is adapted to control the level of depth detail obtained from the object by changing the patterns generated by the pattern generator.

35. The system of claim 23 comprising an endoscope optically coupled to the pattern generator and the detector for projecting the patterns into the body of a patient and for communicating the reflected patterns from the body of the patient to the detector.

36. The system of claim 35 comprising a beam compressor optically coupled to the self-illuminating display and the endoscope for compressing the patterns projected by the display to fit within an optical path of the endoscope.

37. The system of claim 35 wherein the endoscope comprises a laparoscope.

38. A system for real-time structured light depth extraction in an endoscopic surgical environment:

(a) a laser light source for producing a collimated beam of laser light;

(b) a pattern generator optically coupled to the laser light source for presenting a plurality of different structured light patterns, each structured light pattern including a plurality of pixels, when each pattern interacts with the collimated beam of laser light to simultaneously project the plurality of pixels onto an object of interest;

(c) beam expansion optics being optically coupled to the laser light source and the pattern generator for expanding the collimated beam of laser light to illuminate an area of the pattern generator corresponding to the patterns;

(d) an endoscope optically coupled to the pattern generator for communicating the patterns into a patient's body to illuminate an object and for receiving patterns reflected from the object;

(e) beam compression optics being optically coupled to the pattern generator and the detector for reducing a beam width of the projected patterns to a size that fits within an aperture of the endoscope;

(f) a structured light depth extraction camera optically coupled to the object via the endoscope and synchronized with the pattern generator for detecting the reflected patterns and generating signals based on the reflected patterns;

(g) a broadband light source optically coupled to the object via the endoscope for broadband illumination of the object;

(h) a color camera optically coupled to the object via the endoscope for receiving broadband light reflected from the object and for generating signals based on the reflected broadband light; and (i) a real-time structured light depth extraction engine/controller coupled to the cameras and the pattern generator for controlling the projection and detection of patterns for calculating, in real-time, depth and color values for regions of the object based on the signals received from the cameras, and for generating and displaying the image of the object based on the calculated depth values, wherein the projecting of the plurality of pixels onto the object, the calculating of the depth and color values, and the generation of the image of the object are repeated continually to update display of the image in real time, wherein the three dimensional image of the object comprises a synthetic image and wherein the real time structured light depth extraction engine/controller combines the synthetic image with a real image of a scene and displays the combined image.

39. The system of claim 38 wherein the display of the image is updated at a rate of at least about 30 frames per second.

40. A method for laser-based real-time structured light depth extraction comprising:

(a) projecting a beam of laser light from a laser onto a pattern generator;

(b) generating patterns on the pattern generator, each pattern including a plurality of pixels;

(c) altering the beam of laser light using the patterns such that the patterns are projected onto object of interest;

(d) detecting patterns reflected from the object of interest;

(e) calculating depth information relating to the object of interest in real-time based on the reflected patterns;

(f) generating and displaying three-dimensional image of the object based on the calculated depth information; and (g) wherein steps (a)-(f) are continually repeated to update display of the three-dimensional image of the object in real time, wherein the three dimensional image of the object comprises a synthetic image and wherein the method further comprises combining the synthetic image with a real image of a scene and displaying the combined image.

41. The method of claim 40 wherein projecting a beam of laser light onto a pattern generator includes projecting a beam of narrowband laser light onto the pattern generator.

42. The method of claim 41 wherein projecting a beam of narrowband laser light includes projecting a beam of green laser light onto the pattern generator.

43. The method of claim 40 wherein generating patterns includes generating patterns on a transmissive display.

44. The method of claim 40 wherein generating patterns includes generating reflective patterns using a reflective display.

45. The method of claim 40 wherein generating patterns includes generating patterns using a micro-electromechanical system.

46. The method of claim 40 comprising illuminating the object with a broadband light source.

47. The method of claim 46 wherein detecting patterns reflected from the object includes detecting patterns reflected from the object using a high-speed, high-resolution camera and wherein the method further comprises detecting broadband light reflected from the object using the high-speed, high-resolution camera.

48. The method of claim 46 wherein detecting patterns reflected from the object includes detecting the patterns using a high-speed, low-resolution camera and wherein the method further comprises detecting broadband light reflected from the object using a high-resolution, low-speed camera.

49. The method of claim 48 wherein the laser light projecting, the broadband illuminating, the reflected pattern detecting, and the broadband light detecting steps occur asynchronously with respect to each other.

50. The method of claim 48 wherein the laser light projecting, the broadband illuminating, the reflected pattern detecting, and the broadband light detecting steps occur synchronously with respect to each other.

51. The method of claim 40 wherein projecting the patterns onto an object of interest includes projecting the patterns through an endoscope onto an object within a patient's body.

52. The method of claim 51 wherein projecting the patterns through an endoscope includes the projecting the patterns through a laparoscope.

53. The method of claim 51 comprising expanding the beam of laser light to cover a predetermined area of the pattern generator and compressing the patterns reflected from the pattern generator to fit within a diameter of the endoscope.

54. The method of claim 40 wherein calculating depth information in real-time includes rendering depth values at a rate of at least about 30 frames per second.

55. The method of claim 40 wherein the projecting and detecting steps are performed with a photonic efficiency of at least about thirty percent.

56. The method of claim 40 comprising dynamically changing the patterns to increase or decrease the resolution of the depth information.

57. The method of claim 40 wherein the display of the three dimensional image of the object is updated at a rate of at least about 30 frames per second.

58. A method for real-time structured light depth extraction comprising:
(a) projecting patterns from a self-illuminating display onto an object of interest;
(b) detecting patterns reflected from the object of interest;
(c) calculating depth information relating to the object of interest in real-time based on the reflected patterns; and
(d) generating a three-dimensional image of the object based on the calculated depth information.

59. The method of claim 58 wherein projecting patterns onto an object of interest using a self-illuminating display includes projecting patterns from an organic light emitting (OLE) display.

60. The method of claim 58 wherein projecting patterns onto an object of interest using a self-illuminating display includes projecting patterns from the display through an endoscope onto an object inside of a patient's body.

61. The method of claim 58 wherein detecting reflected patterns includes detecting the reflected patterns using a high-speed, low-resolution camera.

62. The method of claim 58 comprising illuminating the object using a broadband light source and detecting broadband light reflected from the object using a high-resolution, low-speed camera.

63. The method of claim 62 comprising combining the depth information with the reflected broadband light to obtain color depth images of the object of interest.

64. The method of claim 58 comprising dynamically changing the patterns to increase or decrease the resolution of the depth information.

* * * * *